United States Patent
Norinobu (10) Patent No.: US 12,161,993 B2
(45) Date of Patent: Dec. 10, 2024

(54) CHROMATOGRAPHY CARRIER, LIGAND-IMMOBILIZING CARRIER, CHROMATOGRAPHY COLUMN, TARGET SUBSTANCE PURIFICATION METHOD, AND CHROMATOGRAPHY CARRIER PRODUCTION METHOD

(71) Applicants: JSR CORPORATION, Minato-ku (JP); JSR LIFE SCIENCES CORPORATION, Minato-ku (JP); JSR Life Sciences, LLC, Sunnyvale, CA (US); JSR MICRO N.V., Leuven (BE)

(72) Inventor: Tomoya Norinobu, Minato-ku (JP)

(73) Assignees: JSR CORPORATION, Minato-ku (JP); JSR LIFE SCIENCES CORPORATION, Minato-ku (JP); JSR Life Sciences, LLC, Sunnyvale, CA (US); JSR MICRO N.V., Leuven (BE)

( * ) Notice: Subject to any disclaimer, the term of this patent is extended or adjusted under 35 U.S.C. 154(b) by 1297 days.

(21) Appl. No.: 16/638,512

(22) PCT Filed: Aug. 23, 2018

(86) PCT No.: PCT/JP2018/031154
§ 371 (c)(1),
(2) Date: Feb. 12, 2020

(87) PCT Pub. No.: WO2019/039545
PCT Pub. Date: Feb. 28, 2019

(65) Prior Publication Data
US 2020/0360894 A1    Nov. 19, 2020

(30) Foreign Application Priority Data
Aug. 23, 2017    (JP) ................ 2017-160120

(51) Int. Cl.
*B01J 20/26* (2006.01)
*B01D 15/10* (2006.01)
(Continued)

(52) U.S. Cl.
CPC ............ *B01J 20/267* (2013.01); *B01D 15/10* (2013.01); *B01D 15/3809* (2013.01);
(Continued)

(58) Field of Classification Search
CPC .... B01J 20/267; B01J 20/285; B01J 20/3085; B01J 20/3219; B01J 20/3208;
(Continued)

(56) References Cited

U.S. PATENT DOCUMENTS 4,948,836 A * 8/1990 Solomon .......... G01N 33/54353
530/816
2005/0029196 A1 2/2005 Rhemrev-Boom
(Continued)

FOREIGN PATENT DOCUMENTS

JP    58-53757 A    3/1983
JP    1-165600 A    6/1989
(Continued)

OTHER PUBLICATIONS

JP2006-111717A_English (Year: 2006).*
(Continued)

*Primary Examiner* — Youngsul Jeong
(74) *Attorney, Agent, or Firm* — Oblon, McClelland, Maier & Neustadt, L.L.P.

(57) ABSTRACT

To provide a chromatography carrier that has excellent antifouling properties and exhibits excellent pressure-resistant performance and shatter-resistant performance.
(Continued)

A chromatography carrier comprising: a polymer having a partial structure containing at least two groups represented by —C(=O)—NH—.

19 Claims, 1 Drawing Sheet

(51) Int. Cl.
*B01D 15/38* (2006.01)
*B01J 20/28* (2006.01)
*B01J 20/285* (2006.01)
*B01J 20/30* (2006.01)
*B01J 20/32* (2006.01)
*C07K 1/22* (2006.01)
*C07K 16/32* (2006.01)

(52) U.S. Cl.
CPC ........ *B01D 15/3828* (2013.01); *B01J 20/285* (2013.01); *B01J 20/3085* (2013.01); *B01J 20/3208* (2013.01); *B01J 20/3219* (2013.01); *C07K 1/22* (2013.01); *C07K 16/32* (2013.01)

(58) Field of Classification Search
CPC ............ B01D 15/3809; B01D 15/3828; B01D 15/10; C07K 1/22; C07K 16/32
See application file for complete search history.

(56) References Cited

U.S. PATENT DOCUMENTS

| | | |
|---|---|---|
| 2006/0084765 A1 | 4/2006 | Muranaka et al. |
| 2006/0240438 A1 | 10/2006 | Nagasaki et al. |
| 2008/0210615 A1 | 9/2008 | Joehnck et al. |
| 2010/0029914 A1 | 2/2010 | Komiya et al. |
| 2017/0043320 A1 | 2/2017 | Momiyama et al. |

FOREIGN PATENT DOCUMENTS

| | | | | |
|---|---|---|---|---|
| JP | 2003-511659 A | | 3/2003 | |
| JP | 2006111717 A | * | 4/2006 | ............ B01J 20/261 |
| JP | 2009-503203 A | | 1/2009 | |
| JP | 5250985 B2 | | 7/2013 | |
| WO | WO 01/25285 A1 | | 4/2001 | |
| WO | WO 2005/010529 A1 | | 2/2005 | |
| WO | WO 2015/119255 A1 | | 8/2015 | |

OTHER PUBLICATIONS

Extended European Search Report issued Mar. 30, 2021 in corresponding European Patent Application No. 18847719.4 8 pages.
International Search Report issued on Nov. 6, 2018 in PCT/JP2018/031154 filed on Aug. 23, 2018, 1 page.

* cited by examiner

CHROMATOGRAPHY CARRIER, LIGAND-IMMOBILIZING CARRIER, CHROMATOGRAPHY COLUMN, TARGET SUBSTANCE PURIFICATION METHOD, AND CHROMATOGRAPHY CARRIER PRODUCTION METHOD

TECHNICAL FIELD

The present invention relates to a chromatography carrier, a carrier having a ligand immobilized thereto, a chromatography column, a purification method of a target substance, and a production method of a chromatography carrier.

BACKGROUND ART

In recent years, expression techniques of target substances such as protein have remarkably advanced in the field of biopharmaceuticals typified by, for example, antibody drugs, and improvement in productivity in purification processes such as chromatography is required accordingly. One way to improve productivity is to reduce a concentration of impurities, such as host cell-derived protein and deoxyribonucleic acid that are mixed in pharmaceutical raw materials, as much as possible with a one-time purification to reduce a purification frequency and the number of purification processes. There is an increasing demand for a filler for chromatography (carrier having a ligand immobilized thereto) capable of achieving this.

In order to improve the impurity removal efficiency in the purification process, it is necessary to improve antifouling properties of a carrier, suppress non-specific adsorption due to a hydrophobic interaction between the impurities and a filler, and suppress the adhesion of impurities to the filler. As an effective means for suppressing such adhesion, it is known to hydrophilize a filler or carrier (Patent Literature 1).

Therefore, as a carrier with increased hydrophilicity, a specific solid-phase carrier (Patent Literature 2) in which insides of pores are immobilized with a water-soluble polymer, a solid-phase carrier formed by performing reversed phase suspension polymerization on hydrophilic monomer such as an acrylamide monomer, or a solid-phase carrier obtained by polymerizing and deprotecting the hydrophilic monomer followed by performing hydrophobic treatment on the hydrophilic monomer with, for example, a protecting group (Patent Literatures 3 to 5) is under development.

CITATION LIST

Patent Literature

Patent Literature 1: WO 2005/010529 A
Patent Literature 2: JP 5250985 B2
Patent Literature 3: JP 2003-511659 A
Patent Literature 4: JP 2009-503203 A
Patent Literature 5: JP 2006-111717 A
Patent Literature 6: WO 2015/119255 A

SUMMARY OF INVENTION

Technical Problem

However, there is a problem that the pressure-resistant performance and the shatter-resistant performance are lowered when the anti-fouling properties of the carrier are improved by the conventionally adopted technology. In the case where the pressure-resistant performance of the carrier is insufficient, compaction may occur and a liquid is allowed to unlikely pass when purification is performed using a column with a large scale. In addition, since a column pressure loss increases and it is difficult to use the carrier under a high linear flow rate, the time required for operation is prolonged. Meanwhile, in the case where the shatter-resistant performance is insufficient, there is a problem that crushing or plastic deformation occurs suddenly when a predetermined flow rate is exceeded, so the carrier cannot be reused.

Under such a background, a carrier in which a crosslinked structure is introduced using 3,6-dioxa-1,8-octanedithiol has been proposed (Patent Literature 6). The carrier has insufficient hydrophilicity, and therefore there is a need to further improve the antifouling properties. In addition, there is also room for improvement in the pressure-resistant performance and the shatter-resistant performance.

Accordingly, the problem to be solved by the present invention is to provide a chromatography carrier that has excellent antifouling properties and exhibits pressure-resistant performance and shatter-resistant performance.

Solution to Problem

Therefore, as a result of intensive studies by the present inventor, it found that both excellent antifouling properties and excellent pressure-resistant performance and shatter-resistant performance are achieved by introducing a partial structure containing at least two groups represented by —C(=O)—NH— into a polymer contained in a chromatography carrier, and the inventor completed the present invention.

That is, the present invention provides the following <1> to <15>.

<1> A chromatography carrier (hereinafter, also referred to as a chromatography carrier of the present invention) containing a polymer (hereinafter, also referred to as a specific polymer) having a partial structure (hereinafter, also referred to as a specific partial structure) containing at least two groups represented by —C(=O)—NH—.

<2> The carrier described in <1>, in which the partial structure is a divalent or more of crosslinked structure represented by the following Formula (1).

$$R^1 (-X^1-X^2-*)_n \qquad (1)$$

[In Formula (1),
$R^1$ represents an n-valent organic group,
$X^1$ represents —C(=O)—NH—,
$X^2$ represents a single bond or a divalent linking group,
n represents an integer of 2 or more, and
* represents a bond,
provided that when n is 2, $R^1$ may be a single bond.]

<3> The carrier described in <1> or <2>, in which the partial structure is a crosslinked structure represented by the following Formula (1-2).

(1-2)

[In Formula (1-2),
$R^2$ represents a single bond or a divalent organic group,
$X^{1a}$ and $X^{1b}$ represent —C(=O)—NH—,
$X^{2a}$ and $X^{2b}$ each independently represent a single bond or a divalent linking group, and
* represents a chemical bond.]

<4> The carrier described in <3>, in which $R^2$ is a divalent hydrocarbon group having 1 to 40 carbon atoms or a group having one or more selected from the group consisting of an ether bond, an amide bond, and an ester bond between carbon-carbon atoms of a divalent hydrocarbon group having 2 to 40 carbon atoms.

<5> The carrier described in <3> or <4>, in which $R^2$ is an alkanediyl group having 1 to 40 carbon atoms or a group having one or more selected from the group consisting of an ether bond, an amide bond, and an ester bond between carbon-carbon atoms of an alkanediyl group having 2 to 40 carbon atoms.

<6> The carrier described in any one of <3> to <5>, in which $X^{2a}$ and $X^{2b}$ are each independently a single bond, —NH—, or —$R^4$—C(=O)O— ($R^4$ represents a divalent organic group).

<7> The carrier described in any one of <1> to <6>, which is a particulate carrier.

<8> The carrier described in any one of <1> to <7>, which is a porous carrier.

<9> The carrier described in any one of <1> to <8>, in which the polymer further has a functional group capable of immobilizing a ligand.

<10> A carrier having a ligand immobilized thereto (hereinafter, also referred to as a carrier having a ligand immobilized thereto of the present invention) in which the ligand is immobilized to the carrier described in any one of <1> to <9>.

<11> The carrier having a ligand immobilized thereto described in <10>, in which the ligand is protein or peptide.

<12> A chromatography column in which the carrier having a ligand immobilized thereto described in <10> or <11> is filled with a column container (hereinafter, also referred to as a chromatography column of the present invention).

<13> A purification method of a target substance (hereinafter, also referred to as a purification method of target substance of the present invention) by chromatography, which comprises using the carrier having a ligand immobilized thereto described in <10> or <11>.

<14> A purification method of a target substance by chromatography, including: brining the carrier having a ligand immobilized thereto described in <10> or <11> into contact with a sample containing a target substance.

<15> A production method of chromatography carrier (hereinafter, also referred to as a production method of a chromatography carrier of the present invention) including: bringing a solid phase having one or more functional group selected from the group consisting of a cyclic ether group, a carboxy group, —C(=O)—O—C(=O)—, a succinimide oxycarbonyl group, a formyl group, and an isocyanate group into contact with a crosslinking agent containing at least two groups represented by —C(=O)—NH— in molecules thereof.

Advantageous Effects of Invention

The chromatography carrier of the present invention has the excellent antifouling properties and exhibits the pressure-resistant performance and the shatter-resistant performance. In addition, it has the large dynamic binding capacity with respect to the target substance when the ligand is immobilized.

Therefore, according to the present invention, it is possible to provide the carrier having a ligand immobilized thereto and the chromatography column that have the excellent antifouling properties, exhibit the excellent pressure-resistant performance and the shatter-resistant performance, and also have the large dynamic binding capacity to the target substance.

DESCRIPTION OF EMBODIMENTS

<Chromatography Carrier>

Figure 1:
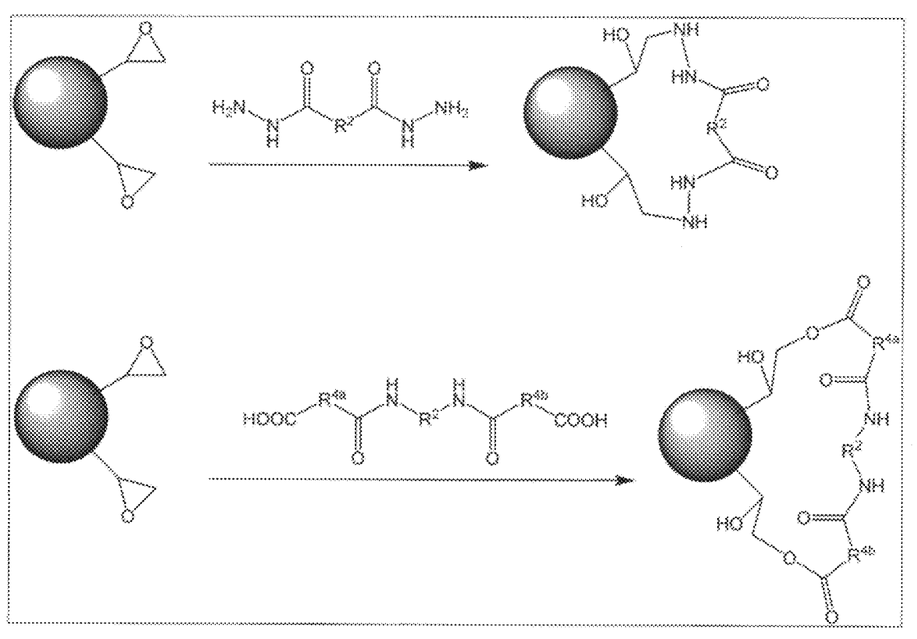
The FIGURE is a diagram showing an example of a chromatography carrier production method of the present invention.

A chromatography carrier of the present invention includes a polymer having a partial structure containing at least two groups represented by —C(=O)—NH—.

As the specific partial structure, a divalent or more of crosslinked structure represented by the following Formula (1) is preferable from the viewpoint of enhancing the desired effect of the present invention.

[In Formula (1),
$R^1$ represents an n-valent organic group,
$X^1$ represents —C(=O)—NH—,
$X^2$ represents a single bond or a divalent linking group,
n represents an integer of 2 or more,
* represents a bond, and
when n is 2, $R^1$ may be a single bond.]

In the Formula (1), the number of carbon atoms of an n-valent organic group represented by $R^1$ is preferably 1 to 60, more preferably 1 to 40, and particularly preferably 1 to 20 from the viewpoint of enhancing the desired effect of the present invention.

n represents an integer of 2 or more, but is preferably 2 to 6, more preferably 2 to 4, still more preferably 2 or 3, and particularly preferably 2 from the viewpoint of enhancing the desired effect of the present invention. Note that n $X^1$ may be the same or different, and n $X^2$ may also be the same or different.

In —C(=O)—NH— represented by $X^1$, a carbon atom in the chemical structure may be bonded to $R^1$ and a nitrogen atom in the chemical structure may be bonded to $X^2$, or the carbon atom in the chemical structure may be bonded to $X^2$ and the nitrogen atom in the chemical structure may be bonded to $R^1$.

As $X^2$, a divalent linking group is preferable from the viewpoint of enhancing the desired effect of the present invention. As the divalent linking group, —NH— or —$R^4$—C(=O)O— is preferable from the viewpoint of enhancing the desired effect of the present invention, and —NH— is particularly preferable. In particular, when $X^2$ is —NH—, the pressure-resistant performance is further improved.

In addition, $R^4$ represents a divalent organic group. Note that in —$R^4$—C(=O)O—, $R^4$ in the chemical structure may be bonded to $X^1$, or an oxygen atom in the chemical structure may be bonded to $X^1$.

Examples of the divalent organic group represented by $R^4$ include a divalent hydrocarbon group or a group having one or more selected from the group consisting of an ether bond, an amide bond, and an ester bond between carbon-carbon atoms of the divalent hydrocarbon group having 2 or more carbon atoms.

When the divalent organic group represented by $R^4$ is the divalent hydrocarbon group, the number of carbon atoms of the divalent organic group is preferably 1 to 20, more preferably 1 to 14, still more preferably 1 to 8, and particularly preferably 1 to 4 from the viewpoint of enhancing the desired effect of the present invention. On the other hand, when the divalent organic group is the "group having one or more selected from the group consisting of an ether bond, an amide bond, and an ester bond between carbon-carbon atoms of the divalent hydrocarbon group having 2 or more carbon atoms", the number of carbon atoms of the divalent hydrocarbon group in such a group is preferably 2 to 20, more preferably 2 to 14, still more preferably 2 to 8, and particularly preferably 2 to 4 from the viewpoint of enhancing the desired effect of the present invention.

Note that the divalent hydrocarbon group represented by $R^4$ and the divalent hydrocarbon group in the "group having one or more selected from the group consisting of an ether bond, an amide bond, and an ester bond between carbon-carbon atoms of the divalent hydrocarbon group having 2 or more carbon atoms" may have a substituent. Examples of the substituent include a halogen atom such as a chlorine atom and a bromine atom, a hydroxy group, and the like. Note that substitution positions and the number of substituents are arbitrary, and when two or more substituents are present, the substituents may be the same or different.

Examples of the divalent hydrocarbon group represented by $R^4$ and the divalent hydrocarbon group in the "group having one or more selected from the group consisting of an ether bond, an amide bond, and an ester bond between carbon-carbon atoms of the divalent hydrocarbon group having 2 or more carbon atoms" include a divalent aliphatic hydrocarbon group, a divalent alicyclic hydrocarbon group, and a divalent aromatic hydrocarbon group, but from the viewpoint of enhancing the desired effect of the present invention, the divalent aliphatic hydrocarbon group is preferable. Note that the divalent aliphatic hydrocarbon group may be linear or branched.

When the divalent organic group represented by $R^4$ is the divalent aliphatic hydrocarbon group, the number of carbon atoms of the divalent organic group is preferably 1 to 20, more preferably 1 to 14, still more preferably 1 to 8, and particularly preferably 1 to 4 from the viewpoint of enhancing the desired effect of the present invention. On the other hand, when the divalent organic group is the "group having one or more selected from the group consisting of an ether bond, an amide bond, and an ester bond between carbon-carbon atoms of the divalent aliphatic hydrocarbon group having 2 or more carbon atoms", the number of carbon atoms of the divalent aliphatic hydrocarbon group in such a group is preferably 2 to 20, more preferably 2 to 14, still more preferably 2 to 8, and particularly preferably 2 to 4 from the viewpoint of enhancing the desired effect of the present invention.

In addition, the divalent aliphatic hydrocarbon group may have an unsaturated bond in molecules thereof, but is preferably an alkanediyl group from the viewpoint of enhancing the desired effect of the present invention. Specific examples of the alkanediyl group include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,1-diyl group, a butane-1,2-diyl group, a butane-1,3-diyl group, a butane-1,4-diyl group, a pentane-1,1-diyl group, a pentane-1,2-diyl group, a pentane-1,3-diyl group, a pentane-1,4-diyl group, a pentane-1,5-diyl group, a hexane-1,1-diyl group, a hexane-1,2-diyl group, a hexane-1,3-diyl group, a hexane-1,4-diyl group, a hexane-1,5-diyl group, a hexane-1,6-diyl group, a heptane-1,7-diyl group, an octane-1,8-diyl group, and the like. Among these, the methane-1,1-diyl group, the ethane-1,2-diyl group, the propane-1,3-diyl group, the butane-1,4-diyl group, the pentane-1,5-diyl group, the hexane-1,6-diyl group, the heptane-1,7-diyl group, and the octane-1,8-diyl group are particularly preferable from the viewpoint of enhancing the desired effect of the present invention.

The number of carbon atoms of the divalent alicyclic hydrocarbon group is preferably 3 to 20, more preferably 3 to 16, still more preferably 3 to 12, and particularly preferably 3 to 8. Specific examples of the divalent alicyclic hydrocarbon group include cycloalkylene groups such as a cyclopropylene group, a cyclobutylene group, a cyclopentylene group, and a cyclohexylene group.

The number of carbon atoms of the divalent aromatic hydrocarbon group has preferably 6 to 18, and more preferably 6 to 12. Specific examples of the divalent aromatic hydrocarbon group include arylene groups such as a phenylene group and a naphthylene group.

Note that a binding site of the divalent alicyclic hydrocarbon group and a binding site of the divalent aromatic hydrocarbon group may be on any carbon on a ring.

As the specific partial structure as described above, from the viewpoint of enhancing the desired effect of the present invention, a crosslinked structure represented by the following Formula (1-2) or (1-3) is preferable, a crosslinked structure represented by the following Formula (1-2) is more preferable, a crosslinked structure represented by the following Formulas (2-1) to (2-6) is still more preferable, and a crosslinked structure represented by the Formulas (2-1) to (2-4) is further still more preferable, a crosslinked structure represented by Formula (2-1) or (2-4) is further even still more preferable, and a crosslinked structure represented by Formula (2-1) is particularly preferable. In the case of the crosslinked structure represented by the Formula (2-1), the pressure-resistant performance is particularly good.

(1-2)

[In Formula (1-2),
$R^2$ represents a single bond or a divalent organic group,
$X^{1a}$ and $X^{1b}$ represent —C(=O)—NH—,
$X^{2a}$ and $X^{2b}$ each independently represent a single bond or a divalent linking group, and
* represents a bond.]

(1-3)

[In the Formula (1-3),
$R^3$ represents an m-valent organic group,
$X^1$ represents —C(=O)—NH—,
$X^2$ represents a single bond or a divalent linking group,
m represents an integer of 3 or more, and
* represents a bond.]

(2-1)

(2-2)

(2-3)

(2-4)

(2-5)

(2-6)

[In the Formulas (2-1) to (2-6), $R^2$ and * have the same meanings as $R^2$ and * in the Formula (1-2), $R^2$ represents a single bond or a divalent organic group, and * represents a bond. In addition, $R^{4a}$ and $R^{4b}$ in Formulas (2-3) and (2-4) each independently represent a divalent organic group.]

Here, each symbol in the Formulas (1-2), (1-3), (2-1) to (2-6) will be described.

$X^{1a}$ and $X^{1b}$ in the Formula (1-2) and $X^1$ in the Formula (1-3) represent —C(=O)—NH—. $X^{1a}$ and $X^{1b}$ in the Formula (1-2) and $X^1$ in the Formula (1-3) have the same meaning as $X^1$ in the above Formula (1).

$X^{2a}$ and $X^{2b}$ in Formula (1-2) and $X^2$ in Formula (1-3) each independently represent a single bond or a divalent linking group. $X^{2a}$ and $X^{2b}$ in Formula (1-2) and $X^2$ in Formula (1-3) have the same meaning as $X^2$ in the above Formula (1), and as the divalent linking group represented by them, —NH— and —$R^4$—C(=O)O— is preferable, and —NH— is particularly preferable. In particular, when $X^2$ is —NH—, the pressure-resistant performance is further improved. Note that $R^4$ is as described above and represents a divalent organic group.

$R^{4a}$ and $R^{4b}$ in Formulas (2-3) and (2-4) each independently represent a divalent organic group. $R^{4a}$ and $R^{4b}$ in Formulas (2-3) and (2-4) have the same meaning as $R^4$ in the above Formula (1).

$R^2$ in Formulas (1-2) and (2-1) to (2-6) represents a single bond or a divalent organic group, but from the viewpoint of enhancing the desired effect of the present invention, the divalent organic group is preferable. The number of carbon atoms of the divalent organic group is preferably 1 to 40, more preferably 1 to 30, still more preferably 1 to 20, and particularly preferably 1 to 10 from the viewpoint of enhancing the desired effect of the present invention.

As the divalent organic group represented by $R^2$, from the viewpoint of enhancing the desired effect of the present invention, the divalent hydrocarbon group, the group having one or more selected from the group consisting of the ether bond, the amide bond, and the ester bond between the carbon-carbon atoms of the divalent hydrocarbon group having 2 or more carbon atoms, and a divalent nitrogen-containing heterocyclic group are preferable, and the divalent hydrocarbon group and the group having one or more selected from the group consisting of the ether bond, the amide bond, and the ester bond between the carbon-carbon atoms of the divalent hydrocarbon group having 2 or more carbon atoms are more preferable. Note that the divalent hydrocarbon group represented by $R^2$, the divalent hydrocarbon group in the "group having one or more selected from the group consisting of an ether bond, an amide bond, and an ester bond between carbon-carbon atoms of the divalent hydrocarbon group having 2 or more carbon atoms", and the divalent nitrogen-containing heterocyclic group may have a substituent. Examples of the substituent include a halogen atom such as a chlorine atom and a bromine atom, a hydroxy group, and the like. Note that substitution positions and the number of substituents are arbitrary, and when two or more substituents are present, the substituents may be the same or different.

When the divalent organic group represented by $R^2$ is the divalent hydrocarbon group, the number of carbon atoms of the divalent organic group is preferably 1 to 40, more preferably 1 to 30, still more preferably 1 to 20, and particularly preferably 1 to 10 from the viewpoint of enhancing the desired effect of the present invention. On the other hand, when the divalent organic group represented by $R^2$ is the "group having one or more selected from the group consisting of an ether bond, an amide bond, and an ester bond between carbon-carbon atoms of the divalent hydrocarbon group having 2 or more carbon atoms", the number of carbon atoms of the divalent hydrocarbon group in such a group is preferably 2 to 40, more preferably 2 to 30, still more preferably 2 to 20, and particularly preferably 2 to 10 from the viewpoint of enhancing the desired effect of the present invention.

Examples of the divalent hydrocarbon group represented by $R^2$ and the divalent hydrocarbon group in the "group having one or more selected from the group consisting of an ether bond, an amide bond, and an ester bond between carbon-carbon atoms of the divalent hydrocarbon group having 2 or more carbon atoms" include a divalent aliphatic hydrocarbon group, a divalent alicyclic hydrocarbon group, and a divalent aromatic hydrocarbon group, but from the viewpoint of enhancing the desired effect of the present invention, the divalent aliphatic hydrocarbon group is preferable. Note that the divalent aliphatic hydrocarbon group may be linear or branched.

When the divalent organic group represented by $R^2$ is the divalent aliphatic hydrocarbon group, the number of carbon atoms of the divalent organic group is preferably 1 to 40, more preferably 1 to 30, still more preferably 1 to 20, further still more preferably 1 to 10, further even still more preferably 1 to 8, and particularly preferably 2 to 6 from the viewpoint of enhancing the desired effect of the present invention. On the other hand, when the divalent organic group represented by $R^2$ is the "group having one or more selected from the group consisting of an ether bond, an amide bond, and an ester bond between carbon-carbon atoms of the divalent aliphatic hydrocarbon group having 2 or more carbon atoms", the number of carbon atoms of the divalent aliphatic hydrocarbon group in such a group is preferably 2 to 40, more preferably 2 to 30, still more preferably 2 to 20, further still more preferably 2 to 10, further even still more preferably 2 to 8, and particularly preferably 2 to 6 from the viewpoint of enhancing the desired effect of the present invention.

In addition, as the "group having one or more selected from the group consisting of an ether bond, an amide bond and an ester bond between carbon-carbon atoms of a divalent aliphatic hydrocarbon group having 2 or more carbon atoms", the group having the ether bond between the carbon-carbon atoms of the divalent aliphatic hydrocarbon group having 2 or more carbon atoms is preferable. For example, $(CH_2)_2$—OC(=O)—$CH_2$— is used.

In addition, the divalent aliphatic hydrocarbon group may have an unsaturated bond in molecules thereof, but is preferably an alkanediyl group from the viewpoint of enhancing the desired effect of the present invention. Specific examples of the alkanediyl group include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,1-diyl group, a butane-1,2-diyl group, a butane-1,3-diyl group, a butane-1,4-diyl group, a pentane-1,1-diyl group, a pentane-1,2-diyl group, a pentane-1,3-diyl group, a pentane-1,4-diyl group, a pentane-1,5-diyl group, a hexane-1,1-diyl group, a hexane-1,2-diyl group, a hexane-1,3-diyl group, a hexane-1,4-diyl group, a hexane-1,5-diyl group, a hexane-1,6-diyl group, a heptane-1,7-diyl group, an octane-1,8-diyl group, and the like. Among these, the methane-1,1-diyl group, the ethane-1,2-diyl group, the propane-1,3-diyl group, the butane-1,4-diyl group, the pentane-1,5-diyl group, the hexane-1,6-diyl group, the heptane-1,7-diyl group, and the octane-1,8-diyl group are particularly preferable from the viewpoint of enhancing the desired effect of the present invention.

The number of carbon atoms of the divalent alicyclic hydrocarbon group is preferably 3 to 20, more preferably 3 to 16, still more preferably 3 to 12, and particularly preferably 3 to 8. Specific examples of the divalent alicyclic hydrocarbon group include cycloalkylene groups such as a cyclopropylene group, a cyclobutylene group, a cyclopentylene group, and a cyclohexylene group.

The number of carbon atoms of the divalent aromatic hydrocarbon group has preferably 6 to 18, and more preferably 6 to 12. Specific examples of the divalent aromatic hydrocarbon group include arylene groups such as a phenylene group and a naphthylene group.

The number of carbon atoms of the divalent nitrogen-containing heterocyclic group is preferably 4 to 18, more preferably 4 to 10, and particularly preferably 4 to 6. Specific examples of the divalent nitrogen-containing heterocyclic group include a pyridinylene group (divalent group derived from a pyridine ring) a pyrimidinylene group (divalent group derived from a pyrimidine ring), and the like.

Note that a binding site of the divalent alicyclic hydrocarbon group, a binding site of the divalent aromatic hydrocarbon group, and a binding site of the divalent nitrogen-containing heterocyclic group may be on any carbon on a ring.

In the Formula (1-3), m represents an integer of 3 or more, but is preferably 3 to 6, more preferably 3 or 4, and particularly preferably 3 from the viewpoint of enhancing the desired effect of the present invention. Note that m $X^1$ may be the same or different, and m $X^2$ may also be the same or different.

When m is 3, $R^3$ is a trivalent organic group, but examples of the trivalent organic group include a trivalent hydrocarbon group. The trivalent hydrocarbon group may have a substituent. Examples of the substituent include the same as described in relation to those represented by the divalent hydrocarbon group.

The number of carbon atoms in the trivalent hydrocarbon group is preferably 1 to 40, more preferably 1 to 30, still more preferably 1 to 20, and particularly preferably 1 to 10.

Examples of the trivalent hydrocarbon group include a trivalent aliphatic hydrocarbon group, a trivalent alicyclic hydrocarbon group, and a trivalent aromatic hydrocarbon group, but the trivalent aliphatic hydrocarbon group and the trivalent alicyclic hydrocarbon group are preferable. Note that a binding site of the trivalent alicyclic hydrocarbon group and a binding site of the trivalent aromatic hydrocarbon group may be on any carbon on a ring.

The number of carbon atoms of the trivalent aliphatic hydrocarbon group is preferably 1 to 40, more preferably 1 to 30, still more preferably 1 to 20, further still more preferably 1 to 10, further even still more preferably 1 to 8, and particularly preferably 2 to 6 from the viewpoint of enhancing the desired effect of the present invention. In addition, the trivalent aliphatic hydrocarbon group may have an unsaturated bond in molecules thereof, but is preferably an alkanetriyl group. Specific examples of the alkanetriyl group include a methane-1,1,1-triyl group, an ethane-1,1,1-triyl group, an ethane-1,1,2-triyl group, a propane-1,2,3-triyl group, a propane-1,2,2-triyl group, and the like.

The number of carbon atoms of the trivalent alicyclic hydrocarbon group has preferably 3 to 20, more preferably 3 to 16, still more preferably 3 to 12, and particularly preferably 3 to 8. Specific examples of the trivalent alicyclic hydrocarbon group include cycloalkanetriyl groups such as a cyclopropanetriyl group, a cyclobutanetriyl group, a cyclopentanetriyl group, and a cyclohexanetriyl group.

Examples of the specific partial structure include a structure derived from a crosslinking agent containing at least two groups represented by —C(=O)—NH— in molecules thereof. As such a crosslinking agent, ones capable of introducing a crosslinked structure by reacting with a functional group capable of immobilizing a ligand together with containing at least two groups represented by —C(=O)—NH— in molecules thereof are preferable. Examples of the crosslinking agent include dicarboxylic acid dihydrazides such as oxalyl dihydrazide, malonic acid dihydrazide, succinic acid dihydrazide, 2,3-dihydroxysuccinic acid dihydrazide, glutaric acid dihydrazide, adipic acid dihydrazide, pimelic acid dihydrazide, octanedioic acid dihydrazide, nonanedioic acid dihydrazide, sebacic acid dihydrazide, dodecanedioic acid dihydrazide, phthalic acid dihydrazide, isophthalic acid dihydrazide, terephthalic acid dihydrazide, and quinolinic acid dihydrazide; tricarboxylic acid trihydrazides such as cyclohexanetricarboxylic acid trihydrazide; (alkylenebisimino) bis (oxoalkanoic acids) such as N1,N1-(ethane-1,2-diyl) bis (succinic monoamide), and the like. One crosslinking agent can be used alone, or two or more crosslinking agents can be used in combination. Among these crosslinking agents, dicarboxylic acid dihydrazides and (alkylenebisimino) bis (oxoalkanoic acids) are preferable, and dicarboxylic acid dihydrazides are more preferable from the viewpoint of enhancing the desired effect of the present invention. When the dicarboxylic acid dihydrazides are used, the pressure-resistant performance is particularly good.

In addition, as a specific polymer, those further having a functional group capable of immobilizing a ligand from the viewpoint of enhancing the desired effect of the present invention are preferable.

Examples of the functional group capable of immobilizing the ligand include one or more functional groups selected from the group consisting of a cyclic ether group, a carboxy group, —C(=O)—O—C(=O)—, a succinimide oxycarbonyl group, a formyl group, and an isocyanate group, but the cyclic ether group is preferable from the viewpoint of enhancing the desired effect of the present invention.

Here, the "cyclic ether group" is preferably a cyclic ether group having 3 to 7 atoms constituting a ring. The cyclic ether group may have an alkyl group as a substituent. Specific examples of the cyclic ether group include the cyclic ether group represented by the following Formulas (3) to (8), and the cyclic ether group represented by the Formula (3), (5) or (8) is preferable, and the cyclic ether group represented by the Formula (3) is more preferable.

(3)

(4)

(5)

(6)

(7)

(8)

[In the Formula, $R^{5a}$, $R^{5b}$, $R^{5c}$, and $R^6$ each independently represent a hydrogen atom or an alkyl group, and * represents a bond.]

The number of carbon atoms of the alkyl group represented by $R^{5a}$, $R^{5b}$, $R^{5c}$, and $R^6$ is preferably 1 to 4 and more preferably 1 or 2. The alkyl group may be linear or branched, and examples thereof include a methyl group, an ethyl group, an n-propyl group, an isopropyl group, an n-butyl group, a sec-butyl group, a tert-butyl group, and the like. In addition, $R^{5a}$, $R^{5b}$, $R^{5c}$, and $R^6$ are preferably a hydrogen atom.

In addition, examples of the specific polymer include those having two or more residues of the functional group capable of immobilizing a ligand, with those in which the two or more residues are crosslinked by a specific partial structure being preferable, and those having two or more residues of the functional group capable of immobilizing a ligand and a functional group capable of immobilizing a ligand, with those in which the two or more residues are crosslinked by a specific partial structure being more preferable.

The residues of the functional group capable of immobilizing the ligand means residues remaining when the functional group capable of immobilizing the ligand is crosslinked by a crosslinking agent. Specific examples of the residue include a divalent group formed by ring-opening a cyclic ether group, —C(=O)—, and —NH—C(=O)—, and from the viewpoint of enhancing the effect, the divalent group formed by ring-opening the cyclic ether group is preferable. As the "cyclic ether group" in the divalent group formed by ring-opening the cyclic ether group, the same those as those exemplified as the functional group capable of immobilizing the ligand are preferable.

The content of the specific partial structure is preferably 0.5 to 50% by mass, more preferably 1 to 40% by mass, and particularly preferably 10 to 35% by mass in the specific polymer from the viewpoint of enhancing the desired effect of the present invention.

A molar ratio of the content (β) of the specific partial structure in the specific polymer to the total content (α) of the functional group capable of immobilizing the ligand in the specific polymer and the residue thereof [(β)/(α)] is preferably 0.01 to 0.8, more preferably 0.05 to 0.7, still more preferably 0.1 to 0.6, and particularly preferably 0.2 to 0.5 from the viewpoint of enhancing the desired effect of the present invention. According to the present invention, the excellent antifouling properties can be obtained even when the molar ratio [(β)/(α)] is 0.2 or more.

Note that the content of each structure in the specific polymer can be measured by, for example, elemental analysis or pyrolysis gas chromatography.

Examples of the specific polymer preferably include those having a structural unit (A) having a functional group capable of immobilizing a ligand and a structural unit (B) having residues of a functional group capable of immobilizing a ligand, in which those in which the residues in the structural unit (B) are crosslinked by a specific partial structure are preferable. As the structural unit (A), a structural unit represented by the following Formula (9) is preferable, and as the structural unit (B), a structural unit represented by the following Formula (10) is preferable.

(9)

[In Formula (9),
$R^8$ represents a hydrogen atom or a methyl group,
$R^9$ represents a single bond or a divalent linking group, and
$Z^1$ represents a functional group capable of immobilizing a ligand.]

(10)

[In the Formula (10),
$R^{10}$ represents a hydrogen atom or a methyl group,
$R^{11}$ represents a single bond or a divalent linking group, $Z^2$ represents a residue of a functional group capable of immobilizing a ligand, and

** represents a bond that is bonded to a specific partial structure.]

Examples of the functional group capable of immobilizing the ligand represented by $Z^1$ in the Formula (9) and the residue of the functional group capable of immobilizing the ligand represented by $Z^2$ in the Formula (10) include the same those as described above. Further, ** in the Formula (10) represents the bond that binds to the specific partial structure, and means that it is crosslinked by the specific partial structure.

Examples of the divalent linking group represented by $R^9$ in the Formula (9) and $R^{11}$ in the Formula (10) include an alkanediyl group, a group having an ether bond between carbon-carbon atoms of an alkanediyl group having 2 or more carbon atoms, an arylene group, —C(=O)O—$R^{12}$-*, —C(=O)NH—$R^{13}$-*, —Ar—$R^{14}$—Ar—$OR^{15}$-*, or the like. Here, Ar represents an arylene group, and * in $R^9$ and $R^{11}$ represents a bond bonded to $Z^1$ or $Z^2$. Examples of the arylene group represented by $R^9$, $R^{11}$, and Ar include a phenylene group, a naphthylene group, and a phenanthrenylene group.

In addition, $R^{12}$ to $R^{15}$ each independently represent an alkanediyl group or a group having an ether bond between carbon-carbon atoms of an alkanediyl group having 2 or more carbon atoms.

The number of carbon atoms of the alkanediyl group represented by $R^9$, $R^{11}$, and $R^{12}$ to $R^{15}$ is preferably 1 to 12, more preferably 1 to 6, and particularly preferably 1 to 3. The alkanediyl group may be linear or branched. Specific examples of the alkanediyl group include a methane-1,1-diyl group, an ethane-1,1-diyl group, an ethane-1,2-diyl group, a propane-1,1-diyl group, a propane-1,2-diyl group, propane-1,3-diyl group, a propane-2,2-diyl group, a butane-1,1-diyl group, a butane-1,2-diyl group, a butane-1,3-diyl group, a butane-1,4-diyl group, a pentane-1,1-diyl group, a pentane-1,2-diyl group, a pentane-1,3-diyl group, a pentane-1,4-diyl group, a pentane-1,5-diyl group, a hexane-1,1-diyl group, a hexane-1,2-diyl group, a hexane-1,3-diyl group, a hexane-1,4-diyl group, a hexane-1,5-diyl group, a hexane-1,6-diyl group, a heptane-1,7-diyl group, an octane-1,8-diyl group, and the like.

As the "group having an ether bond between carbon-carbon atoms of an alkanediyl group having 2 or more carbon atoms" represented by $R^9$, $R^{11}$, and $R^{12}$ to $R^{15}$, a group represented by —$R^a(OR^b)_pOR^c$— is preferable ($R^a$, $R^b$, and $R^c$ each independently represent an alkanediyl group having 1 to 4 carbon atoms, and p represents an integer of 0 to 30.).

The alkanediyl group represented by $R^a$, $R^b$, and $R^c$ may be linear or branched. Specific examples of the alkanediyl group include a methane-1,1-diyl group, an ethane-1,1-diyl group, an ethane-1,2-diyl group, propane-1,1-diyl group, a propane-1,2-diyl group, a propane-1,3-diyl group, a propane-2,2-diyl group, a butane-1,1-diyl group, a butane-1,2-diyl group, a butane-1,3-diyl group, and a butane-1,4-diyl group. p is preferably an integer of 0 to 20, more preferably an integer of 0 to 10, still more preferably an integer of 0 to 5, and particularly preferably 0. Note that when p is an integer of 2 to 30, p $R^b$ may be the same or different. Preferable specific examples of the group having the ether bond between the carbon-carbon atoms of the alkanediyl group having 2 or more carbon atoms include a $C_{1-4}$ alkanediyloxy $C_{1-4}$ alkanediyl group.

Note that the alkanediyl group represented by $R^9$, $R^{11}$, and $R^{12}$ to $R^{15}$ and the group having an ether bond between the carbon-carbon atoms of the alkanediyl group may have a substituent. Examples of the substituent include a hydroxy group.

Among $R^9$ and $R^{11}$ as described above, —C(=O)O—$R^{12}$-* is particularly preferable from the viewpoint of easy production of the specific polymer.

As the monomer constituting the structural unit (A) or the structural unit (B), a monomer having a functional group capable of immobilizing a ligand and a polymerizable unsaturated group is preferable. Examples of the monomer include (meth)acrylate-based monomers having a cyclic ether group such as glycidyl(meth)acrylate, 3-oxiranylpropyl(meth)acrylate, 4-oxiranylbutyl(meth)acrylate, 5-oxiranylpentyl(meth)acrylate, 6-oxiranylhexyl(meth)acrylate, 7-xiranylheptyl(meth)acrylate, 8-oxiranyloctyl(meth)acrylate, (3-methyloxiranyl) methyl(meth)acrylate, 4-hydroxybutyl(meth)acrylate glycidyl ether, glycerin mono(meth) acrylate glycidyl ether, 3,4-epoxycyclohexylmethyl(meth) acrylate, 3,4-epoxycyclohexylethyl(meth)acrylate, 3,4-epoxycyclohexylpropyl(meth)acrylate, α-(meth)acrylic-ω-glycidyl polyethylene glycol, and tetrahydrofurfuryl(meth) acrylate; aromatic vinyl-based monomers having a cyclic ether group such as (vinylbenzyl) glycidyl ether, (isopropenylbenzyl) glycidyl ether, (vinylphenethyl) glycidyl ether, (vinylphenylbutyl) glycidyl ether, (vinylbenzyloxyethyl) glycidyl ether, (vinylphenyl) glycidyl ether, (isopropenylphenyl) glycidyl ether, and 1,2-epoxy-3-(4-vinylbenzyl) propane; allyl ether-based monomers having a cyclic ether group such as allyl glycidyl ether; (meth)acrylate-based monomers having an isocyanate group such as isocyanatoethyl(meth)acrylate;(meth)acrylic acid, 3,4-epoxy-1-butene, and 3,4-epoxy-3-methyl-1-butene in addition to unsaturated dicarboxylic acid anhydride-based monomers such as maleic anhydride, methyl maleic anhydride, and glutaconic anhydride, and the like. These monomers can be used alone or in combination of two or more.

Among these monomers, the (meth)acrylate-based monomer having a cyclic ether group is preferable and the glycidyl(meth)acrylate is particularly preferable from the viewpoint of enhancing the desired effect of the present invention.

The total content ratio of the structural units (A) and (B) in the specific polymer is preferably 100 to 1500 parts by mass, and more preferably 100 to 1000 parts by mass with respect to 100 parts by mass of the specific partial structure.

In addition, the specific polymer may have a structural unit in addition to the specific partial structure and the structural units (A) and (B). Examples of the monomer constituting such a structural unit (hereinafter also referred to as other monomers) include polymerizable unsaturated group-containing monomers having no functional group capable of immobilizing a ligand. The other monomers are roughly classified into non-crosslinkable monomers and crosslinkable monomers, and one of these may be used or used in combination. Note that according to the present invention, even when monomers that do not contain a hydrophilic group such as, a hydroxy group are used as the other monomers, it is possible to satisfy the desired effects of the present invention such as the antifouling properties and it is possible to apply for a composition of a wide range of monomers.

Examples of the non-crosslinkable monomers include a (meth)acrylate-based non-crosslinkable monomer, a (meth) acrylamide-based non-crosslinkable monomer, an aromatic vinyl-based non-crosslinkable monomer, a vinyl ketone-based non-crosslinkable monomer, a (meth)acrylonitrile non-crosslinkable monomer, an N-vinylamide-based non-crosslinkable monomer, and the like. These can be used alone or in combination of two or more. Among the non-crosslinkable monomers, the (meth)acrylate-based non-crosslinkable monomer and the aromatic vinyl-based non-crosslinkable monomers are preferable.

Examples of the (meth)acrylate-based non-crosslinkable monomer include methyl(meth)acrylate, ethyl(meth)acrylate, n-butyl(meth)acrylate, 4-tert-butyl(meth)acrylate, and isobutyl(meth)acrylate, n-octyl(meth)acrylate, 2-ethylhexyl (meth)acrylate, cyclohexyl(meth)acrylate, methoxyethyl (meth)acrylate, hydroxyethyl(meth)acrylate, hydroxypropyl (meth)acrylate, glycerol mono(meth)acrylate, trimethylolethane mono(meth)acrylate, trimethylolpropane mono(meth)acrylate, butanetriol mono(meth)acrylate, polyethylene glycol mono(meth)acrylate, methoxypolyethylene glycol(meth)acrylate, pentaerythritol mono(meth)acrylate, dipentaerythritol mono(meth)acrylate, inositol mono(meth) acrylate, and the like. These can be used alone or in combination of two or more.

Examples of the (meth)acrylamide-based non-crosslinkable monomer include(meth)acrylamide, dimethyl(meth)acrylamide, hydroxyethyl(meth)acrylamide, (meth)acryloylmorpholine, diacetone(meth)acrylamide, and the like. These can be used alone or in combination of two or more.

Examples of the aromatic vinyl-based non-crosslinkable monomer include styrenes such as styrene, α-methylstyrene, halogenated styrene, 4-methylstyrene, 2,4-dimethylstyrene, 2,4,6-trimethylstyrene, ethyl vinyl benzene, 4-isopropylstyrene, 4-n-butylstyrene, 4-isobutylstyrene, and 4-tert-butylstyrene; vinylnaphthalenes such as 1-vinylnaphthalene and 2-vinylnaphthalene, and the like. These can be used alone or in combination of two or more.

Examples of the vinyl ketone-based non-crosslinkable monomer include ethyl vinyl ketone, propyl vinyl ketone, and isopropyl vinyl ketone. These can be used alone or in combination of two or more.

Examples of the (meth)acrylonitrile-based non-crosslinkable monomer include acrylonitrile and methacrylonitrile. These can be used alone or in combination of two or more.

Examples of the N-vinylamide-based non-crosslinkable monomer include N-vinylacetamide and N-vinylpropionamide. These can be used alone or in combination of two or more.

The content ratio of the structural unit composed of the non-crosslinkable monomer in the specific polymer is preferably 1 to 500 parts by mass and more preferably 1 to 100 parts by mass with respect to 100 parts by mass of the specific partial structure.

Examples of the crosslinkable monomer include a (meth)acrylate-based crosslinkable monomer, an aromatic vinyl-based crosslinkable monomer, an allyl-based crosslinkable monomer, and the like. These can be used alone or in combination of two or more. As the crosslinkable monomer, a bifunctional to pentafunctional crosslinkable monomer is preferable, and a bifunctional or trifunctional crosslinkable monomer is more preferable. Among the crosslinkable monomers, the (meth)acrylate-based crosslinkable monomer and aromatic vinyl-based crosslinkable monomer are preferable.

Examples of the (meth)acrylate-based crosslinkable monomer include ethylene glycol di(meth)acrylate, diethylene glycol di(meth)acrylate, triethylene glycol di(meth) acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, 1,4-butanediol di(meth)acrylate, 1,6-hexanediol di(meth)acrylate, glycerin di(meth)acrylate, trimethylolethane di(meth)acrylate, trimethylolpropane di(meth)acrylate, trimethylolpropane tri (meth)acrylate, butanetriol di(meth)acrylate, pentaerythritol di(meth)acrylate, pentaerythritol tri(meth)acrylate, pentaerythritol tetra(meth)acrylate, glucose di(meth)acrylate, glucose tri(meth)acrylate, glucose tetra(meth)acrylate, dipentaerythritol di(meth)acrylate, dipentaerythritol tri (meth)acrylate, dipentaerythritol tetra(meth)acrylate, dipentaerythritol penta(meth)acrylate, inositol di(meth)acrylate, inositol tri(meth)acrylate, inositol tetra(meth)acrylate, mannitol di(meth)acrylate, mannitol tri(meth)acrylate, mannitol tetra(meth)acrylate, mannitol penta(meth)acrylate, and the like. These can be used alone or in combination of two or more.

Examples of the aromatic vinyl-based crosslinkable monomer include divinylbenzene, trivinylbenzene, divinyltoluene, divinylxylene, divinylethylbenzene, divinylnaphthalene, and the like. These can be used alone or in combination of two or more.

Examples of the allyl-based crosslinkable monomer include diallyl phthalate, diallyl isophthalate, diallyl terephthalate, diallyl maleate, diallyl fumarate, diallyl itaconate, diallyl trimellitate, triallyl trimellitate, triallyl cyanurate, diallyl isocyanurate, triallyl isocyanurate, and the like. These can be used alone or in combination of two or more.

Further, examples of the crosslinkable monomer may include dehydration condensation reaction products of amino alcohols such as diaminopropanol, trishydroxymethylaminomethane, and glucosamine with (meth) acrylic acid, and conjugated diolefins such as butadiene and isoprene, in addition to those exemplified above.

The content ratio of the structural unit composed of the crosslinkable monomer in the specific polymer is preferably 1 to 1000 parts by mass, and more preferably 10 to 500 parts by mass with respect to 100 parts by mass of the specific partial structure.

The specific polymer is not particularly limited as long as it has a specific partial structure, and may be a natural polymer or a synthetic polymer composed of polysaccharides such as agarose, dextran, and cellulose, but the synthetic polymer is preferable. In addition, the specific polymer is preferably a water-insoluble polymer.

In addition, the content of the specific polymer is preferably 80 to 100% by mass, more preferably 90 to 100% by mass, and particularly preferably 99 to 100% by mass in the chromatography carrier of the present invention.

In addition, the chromatography carrier of the present invention may be any form that can be used as a support (solid phase carrier). Examples of such forms of the chromatography carrier include particulates, monoliths, plates, membranes (including hollow fibers), fibers, cassettes, chips, and the like, and are preferably particulates. In addition, the chromatographic support of the present invention is preferably a porous carrier such as porous particles. In addition, as the porous particles, porous polymer particles are preferable.

In addition, when the chromatography carrier of the present invention is a particulate carrier, the average particle diameter (volume average particle diameter) is preferably 20 to 150 μm and more preferably 40 to 100 μm from the viewpoint of the pressure-resistant performance and the shatter-resistant performance. Further, a coefficient of variation of the average particle diameter is preferably 40% or less and more preferably 30% or less.

In addition, a specific surface area of the chromatography carrier of the present invention is preferably 1 to 500 m$^2$/g and more preferably 10 to 300 m$^2$/g.

In addition, a volume average pore diameter of the chromatography carrier of the present invention is preferably 10 to 300 nm.

Note that the average particle diameter, the coefficient of variation, the specific surface area and the volume average pore diameter can be measured by laser diffraction/scattered particle diameter distribution measurement or the like.

<Chromatography Carrier Production Method>

A chromatography carrier of the present invention can be produced by appropriately combining conventional methods, but can be simply and efficiently produced by a method including a step of bringing a solid phase having one or more functional groups selected from the group consisting of a cyclic ether group, a carboxy group, —C(=O)—O—C(=O)—, a succinimide oxycarbonyl group, a formyl group, and an isocyanate group into contact with a crosslinking agent containing at least two groups represented by —C(=O)—NH— in a molecule thereof.

Specific examples of the above production method include a method including (step 1) obtaining a solid phase such as raw material particles according to a conventional method, and (step 2) bringing the obtained solid phase into contact with a crosslinking agent containing at least two groups represented by C(=O)—NH— in a molecule thereof as illustrated in the FIGURE.

Hereafter, each of the steps is described in detail.

(Step 1)

Step 1 is a step of (co)polymerizing a monomer (hereinafter, also referred to as a functional group-containing monomer) having one or more functional groups selected from the group consisting of a cyclic ether group, a carboxy group, —C(=O)—O—C(=O)—, a succinimide oxycarbonyl group, a formyl group, and an isocyanate group to obtain a solid phase having the functional group. The (co)polymerization method is preferably suspension polymerization.

Examples of the functional group-containing monomer include those exemplified as monomers constituting structural units (A) and (B). In addition, the functional group-containing monomer may be copolymerized with other monomers (non-crosslinkable monomer and crosslinkable monomer).

The total amount of the functional group-containing monomer is preferably from 1 to 99 parts by mass, more preferably from 20 to 95 parts by mass, and still more preferably 40 to 90 parts by mass with respect to 100 parts by mass of the total amount of monomers used in step 1, from the viewpoint of enhancing the desired effect of the present invention.

The total amount of the crosslinkable monomer used is preferably 1 to 70 parts by mass, more preferably 3 to 60 parts by mass, and particularly preferably 5 to 50 parts by mass with respect to 100 parts by mass of the total amount of monomers used in step 1 from the viewpoint of enhancing the desired effect of the present invention.

In addition, when the non-crosslinkable monomer is used, the total amount used is a residual amount other than a functional group-containing monomer and a crosslinkable monomer.

In addition, examples of the specific method of step 1 include a method for dissolving a polymerization initiator in a mixed solution (monomer solution) containing a monomer and, if necessary, a porosity forming agent, suspending the dissolved solution in an aqueous medium, and heating the suspended solution to a predetermined temperature for polymerization, a method for dissolving a polymerization initiator in a mixed solution (monomer solution) containing a monomer and, if necessary, a porosity forming agent and adding the dissolved solution to an aqueous medium heated to a predetermined temperature for polymerization, a method for suspending a mixed solution (monomer solution) containing a monomer, and, if necessary, a porosity forming agent in an aqueous medium, heating the suspended solution to a predetermined temperature, adding a polymerization initiator to the heated suspended solution for polymerization, or the like.

As the polymerization initiator, a radical polymerization initiator is preferable. Examples of the radical polymerization initiator include an azo-based initiator, a peroxide-based initiator, a redox-based initiator, and the like, and specific examples thereof include azobisisobutyronitrile, methyl azobisisobutyrate, azobis-2,4-dimethylvaleronitrile, benzoyl peroxide, di-tert-butyl peroxide, benzoyl peroxide-dimethylaniline, and the like. The total amount of the polymerization initiator used is usually about 0.01 to 10 parts by mass with respect to 100 parts by mass of the total amount of monomers.

The porosity forming agent is used for producing porous particles, and is present together with a monomer in the polymerization in oil droplets, and has a role of forming pores as a non-polymerized component. The porosity forming agent is not particularly limited as long as it can be easily removed on the porous surface, and examples thereof include a linear polymer and the like that are soluble in various organic solvents or mixed monomers, and both of the organic solvent or the mixed monomer may be used together.

Examples of the porosity forming agent include aliphatic hydrocarbons such as hexane, heptane, octane, nonane, decane, and undecane; alicyclic hydrocarbons such as cyclopentane and cyclohexane; aromatic hydrocarbons such as benzene, toluene, xylene, naphthalene, and ethylbenzene; halogenated hydrocarbons such as carbon tetrachloride, 1,2-dichloroethane, tetrachloroethane, and chlorobenzene; aliphatic alcohols such as butanol, pentanol, hexanol, heptanol, 4-methyl-2-pentanol, and 2-ethyl-1-hexanol; alicyclic alcohols such as cyclohexanol; aromatic alcohols such as 2-phenylethyl alcohol and benzyl alcohol; ketones such as diethyl ketone, methyl isobutyl ketone, diisobutyl ketone, acetophenone, 2-octanone, and cyclohexanone; ethers such as dibutyl ether, diisobutyl ether, anisole, and ethoxybenzene; and linear polymers such as a homopolymer of a non-crosslinkable vinyl monomer in addition to esters such as isopentyl acetate, butyl acetate, 3-methoxybutyl acetate, and diethyl malonate. The porosity forming agent can be used alone or in a mixture of two or more.

The total amount of the porous agent used is usually about 40 to 600 parts by mass with respect to 100 parts by mass of the total amount of monomers.

Examples of the aqueous medium include a water-soluble polymer aqueous solution and the like, and examples of the water-soluble polymer include hydroxyethyl cellulose, polyvinyl alcohol, carboxymethyl cellulose, polyvinyl pyrrolidone, starch, gelatin, and the like.

The total amount of the aqueous medium used is usually about 200 to 7000 parts by mass with respect to 100 parts by mass of the total amount of monomers.

In addition, when water is used as a dispersion medium of the aqueous medium, for example, dispersion stabilizers such as sodium carbonate, calcium carbonate, sodium sulfate, calcium phosphate, and sodium chloride may be used.

In step 1, various surfactants including anionic surfactants such as alkyl sulfate ester salt, alkylaryl sulfate ester salt, alkyl phosphate ester salt, and fatty acid salt may be used. In addition, polymerization inhibitors such as nitrites such as sodium nitrite, iodide salts such as potassium iodide, tert-butylpyrocatechol, benzoquinone, picric acid, hydroquinone, copper chloride, and ferric chloride can also be used. In addition, a polymerization preparation agent such as dodecyl mercaptan may be used.

The polymerization temperature in step 1 may be determined according to the polymerization initiator, but is usually about 2 to 100° C., and when the azobisisobutyronitrile is used as the polymerization initiator, the polymerization temperature is preferably 50 to 100° C. and more preferably 60 to 90° C. In addition, a polymerization time is usually 5 minutes to 48 hours and preferably 10 minutes to 24 hours.

(Step 2)

Step 2 is a step of adding and reacting a crosslinking agent containing at least two groups represented by —C(=O)—NH— in molecules thereof to a part of the functional group derived from the functional group-containing monomer and introducing the specific partial structure derived from the crosslinking agent. Thereby, the residues of the functional group are crosslinked by the specific partial structure.

Examples of the crosslinking agent used in step 2 include those exemplified above as the crosslinking agent containing at least two groups represented by —C(=O)—NH— in the molecules thereof, and those containing at least two groups represented by —C(=O)—NH— in the molecules thereof and reacting with the functional group capable of immobilizing the ligand to be able to introduce the crosslinked structure are preferable.

When the solid phase has a cyclic ether group, specifically, a crosslinking agent containing at least two groups represented by —C(=O)—NH—NH$_2$ as a crosslinkable group in the molecules thereof, a crosslinking agent containing at least two groups represented by —C(=O)—NH— in the molecules thereof and at least two carboxy groups in the molecules thereof as a crosslinkable group, and the like can be used.

When the solid phase has a carboxy group, —C(=O)—O—C(=O)—, a succinimide oxycarbonyl group, and a formyl group, specifically, a crosslinking agent or the like containing at least two groups represented by —C(=O)—NH—NH$_2$ as a crosslinkable group can be used.

When the solid phase has an isocyanate group, specifically, a crosslinking agent or the like containing at least two groups represented by —C(=O)—NH—NH$_2$ in the molecules thereof as a crosslinkable group can be used.

In addition, one crosslinking agent can be used alone, or two or more crosslinking agents can be used in combination.

The total amount of the crosslinking agent used is preferably 0.01 to 0.8 molar equivalent, more preferably 0.05 to 0.7 molar equivalent, still more preferably 0.1 to 0.6 molar equivalent, and particularly preferably 0.2 to 0.5 molar equivalent with respect to 1 mol of the functional group derived from the functional group-containing monomer from the viewpoint of enhancing the desired effect of the present invention. According to the present invention, the excellent antifouling properties can be obtained even when the total amount of crosslinking agents used is 0.2 molar equivalent or more.

Step 2 may be performed in the presence of a basic catalyst. Examples of the basic catalyst include triethylamine, N, N-dimethyl-4-aminopyridine, diisopropylethylamine, and the like, and one type thereof can be used alone, or two or more types can be used in combination.

A reaction time in step 2 is not particularly limited, but is usually about 0.5 to 72 hours and preferably 0.5 to 48 hours. A reaction temperature may be appropriately selected below a boiling point of a solvent, but is usually about 2 to 100° C.

In addition, the reaction products obtained at each of the steps may be purified with separation means, such as distillation, extraction, and washing.

The chromatography carrier of the present invention that can be produced as described above has the high hydrophilicity and the excellent antifouling properties, and exhibits the pressure-resistant performance and the shatter-resistant performance. In addition, the dynamic binding capacity with respect to the target substance when the ligand is immobilized increases. Furthermore, the effects can be obtained regardless of the monomer composition, and the production is simple.

The chromatography carrier of the present invention is particularly useful as an affinity chromatography carrier.

<Ligand-Immobilizing Carrier>

The carrier having a ligand immobilized thereto (ligand-immobilizing carrier) of the present invention is obtained by immobilizing a ligand on the chromatography carrier of the present invention. That is, the chromatography carrier of the present invention is used as a support (solid phase carrier). As the carrier used as the support, a carrier including a polymer having a specific partial structure and a functional group capable of immobilizing a ligand is preferable from the viewpoint of enhancing the desired effect of the present invention.

The ligand may be a molecule that binds to a target substance, but examples thereof include proteins such as protein A, protein G, and avidin; peptides such as insulin; nucleic acids such as DNA and RNA; enzymes; chelate compounds such as iminodiacetic acid; antibodies; antigens; hormones; carbohydrates such as heparin, Lewis X, and ganglioside; receptors; Aptamer; vitamins such as biotin and its derivatives; metal ions; low molecular weight compounds such as 2-aminophenylboronic acid, 4-aminobenzamidine, and glutathione in addition to synthetic dyes. In addition, although all the ligands exemplified above may be used, the fragment obtained by a recombinant, an enzyme treatment, and the like may be used. Further, it may be an artificially synthesized peptide or peptide derivative.

Among the ligands, proteins, peptides, nucleic acids, enzymes, and chelate compounds are preferable, proteins and peptides are more preferable, and proteins are particularly preferable. Among the antibody affinity ligands using the target substance as the antibody, the immunoglobulin-binding protein is particularly preferable.

Examples of the antibody affinity ligands include peptide ligands, protein ligands, and chemically synthesized ligands (synthetic compounds), and are preferably the peptide ligands or the protein ligands. Among them, protein A, protein G, protein L, protein H, protein D, protein Arp, protein FcγR, antibody-binding synthetic peptide ligands, and related substances thereof are preferable, protein A, protein G, protein L, and related substances thereof are more preferable, and protein A and related substances thereof are particularly preferable.

The immobilized amount of the ligand is preferably 10 to 300 mg, more preferably 25 to 150 mg per 1 g of a dry weight of the chromatography carrier from the viewpoint of dynamic binding capacity. The immobilized amount of the ligand may be measured by methods similar to Examples described below.

The ligand may be immobilized to the carrier in the same manner as in a conventional method. Examples of the ligand immobilizing method include a method of binding a ligand to a functional group capable of immobilizing a ligand. This method may be performed with reference to the descriptions in, for example, WO 2015/119255 A and WO 2015/041218 A. Specific examples of the method include a method for binding a cyclic ether group, a carboxy group, —C(=O)—O—C(=O)—, a formyl group, or the like of a carrier to an amino group of a ligand or the like.

In addition, the ligand may be immobilized by a method for controlling an orientation of a ligand (U.S. Pat. No. 6,399,750, Ljungquist C. et al., REur. J. Biochem., 1989, volume 186, pp. 557-561), a method for immobilizing a ligand on a carrier via a linker (spacer) (U.S. Pat. No. 5,260,373, JP 2010-133733 A, and JP 2010-133734 A), a method for accumulating a ligand on a carrier with an associative group (JP 2011-256176 A), and the like may be used.

In addition, the carrier on which the ligand is immobilized may be brought into contact with thiol compounds such as methanethiol and thioglycerol to ring-open an unreacted functional group. This processing may be performed with reference to the description in WO 2015/119255 A.

The carrier having a ligand immobilized thereto of the present invention has the excellent antifouling properties, the excellent pressure-resistant performance, and the shatter-resistant performance, and has a large dynamic binding capacity for a target substance.

The carrier having a ligand immobilized thereto of the present invention is suitable for use in chromatography and particularly suitable for use in affinity chromatography.

<Chromatography Column>

The chromatography column of the present invention is a column container packed with the carrier having ligand immobilized thereto of the present invention.

The chromatography column of the present invention is suitable for use in affinity chromatography.

<Target Substance Purification Method>

The target substance purification method of the present invention is a method of purifying a target substance by chromatography, and uses the carrier having ligand immobilized thereto of the present invention.

The target substance purification method of the present invention may be performed according to the conventional method except that the carrier having ligand immobilized thereto of the present invention is used, but includes a step of bringing the carrier having ligand immobilized thereto of the present invention into contact with a sample containing the target substance. In addition, the method may further include a step of eluting the target substance trapped on the carrier by the step. In the elution step, a dissociation solution that dissociates the ligand and the target substance is usually used.

In addition, the purification may be performed using the chromatography column of the present invention. Examples of the method include a method including a step of passing a sample containing a target substance through the chromatography column of the present invention, which may further include an elution step as described above.

Examples of the target substance in the present invention include antigens; antibodies such as monoclonal antibodies and polyclonal antibodies; cells (normal cells; cancer cells such as colon cancer cells and circulating cancer cells in a blood); nucleic acids such as DNA and RNA, and biologically related substances such as proteins, peptides, amino acids, sugars, polysaccharides, lipids, and vitamins, and may be drugs that are drug targets, and low molecular compounds such as biotin.

EXAMPLES

Hereinafter, although the present invention is described in detail with reference to Examples, the present invention is not limited to these Examples.

Example 1

(1) 2.69 g of polyvinyl alcohol (PVA-217 manufactured by Kuraray Co., Ltd.) was added to 448 g of pure water, polyvinyl alcohol was dissolved by heating and stirring and cooled, and then 0.045 g of sodium dodecyl sulfate (manufactured by Wako Pure Chemical Industries, Ltd.) was added and stirred to prepare an aqueous solution S.

Meanwhile, a monomer composition consisting of 3.63 g of divinylbenzene (manufactured by Wako Pure Chemical Industries, Ltd.), 0.36 g of 1-ethyl-4-vinylbenzene (manufactured by ChemSamp Co.), and 14.15 g of glycidyl methacrylate (manufactured by MITSUBISHI GAS CHEMICAL COMPANY, INC.) was dissolved in 29.38 g of 2-octanone (manufactured by Toyo Gosei Co., Ltd.) to prepare a monomer solution.

Next, the total amount of the aqueous solution S was put into a separable flask, a thermometer, a stirring blade and a cooling pipe were attached and set in a hot water bath, and stirring was started in a nitrogen atmosphere. When the total amount of the monomer solution was put into a separable flask, the separable flask was heated by a hot water bath, and an internal temperature of the separable flask reached to 85° C., 1.34 g of 2,2'-azoisobutyronitrile (manufactured by Wako Pure Chemical Industries, Ltd.) was added thereto, and then the internal temperature thereof was maintained at 86° C.

(2) Thereafter, the mixture was stirred for 3 hours while maintaining the temperature at 86° C. Next, the reaction solution was cooled, filtered and washed with pure water and ethanol. The washed particles were dispersed in pure water, and the decantation was conducted three times to remove small particles. Next, the particles were dispersed in pure water so that the concentration of the particles was 10% by mass, and as a result, a porous particle dispersion was obtained. The porous particles contained in this dispersion are referred to as "porous carrier 1".

(3) Thereafter, 0.956 g of adipic acid dihydrazide (manufactured by Tokyo Chemical Industry Co., Ltd.) and 1.418 g of diisopropylethylamine were added to 100 g of the porous particle dispersion, and the mixture was heated to 70° C. and stirred for 8 hours while being maintained at 70° C. Next, the reaction solution was cooled, filtered and washed with pure water and ethanol. Next, the particles were dispersed in pure water so that the concentration of the particles was 10% by mass, and as a result, a porous crosslinked particle dispersion was obtained. The porous crosslinked particles contained in this dispersion are referred to as "chromatography carrier V1".

(4) Next, 0.15 g of modified protein A (rSPA manufactured by Repligen Corporation) was dissolved in 40 mL of 1.2 M sodium sulfate/0.1 M sodium phosphate buffer (pH 6.6) to obtain a protein A solution, and a porous crosslinked particle dispersion (corresponding to 1 g in terms of dry particle mass) was added to the protein A solution. The dispersion was shaken and stirred at 25° C. for 10 hours to immobilize protein A to the particles.

Next, the produced protein A-immobilized particles are dispersed in 40 mL of 1.0 M α-thioglycerol (manufactured by Tokyo Chemical Industry Co., Ltd.)/0.1 M sodium sulfate (pH 8.3) and shaken and stirred at 25° C. for 17 hours, such that a ring-opening of the unreacted epoxy group was conducted. Further, the obtained protein A-immobilized particles in which the unreacted epoxy group is ring-opening were washed with 0.1 M sodium phosphate buffer (pH 6.6), 0.1 M sodium hydroxide aqueous solution, and 0.1 M sodium citrate buffer (pH 3.2) to obtain a filler-containing liquid for affinity chromatography. The filler contained in this liquid is referred to as "carrier having ligand immobilized thereto W1".

Example 2

A porous crosslinked particle dispersion was obtained by performing the same operation as the steps (1) to (3) in Example 1 except that in step (3) of Example 1, the amount of adipic acid dihydrazide used was changed to 2.390 g and the amount of diisopropylethylamine used was changed to 3.546 g. The porous crosslinked particles contained in this dispersion are referred to as "chromatography carrier V2".

Next, the same step as step (4) of Example 1 was performed to obtain a filler-containing liquid for affinity chromatography. The filler contained in this liquid is referred to as "carrier having ligand immobilized thereto W2".

Example 3

A porous crosslinked particle dispersion was obtained by performing the same operation as in steps (1) to (3) in Example 1 except that in step (3) of Example 1, the amount of adipic acid dihydrazide used was changed to 3.823 g and the amount of diisopropylethylamine used was changed to 5.673 g. The porous crosslinked particles contained in this dispersion are referred to as "chromatography carrier V3".

Next, the same step as step (4) of Example 1 was performed to obtain a filler-containing liquid for affinity chromatography. The filler contained in this liquid is referred to as "carrier having ligand immobilized thereto W3".

Example 4

A porous crosslinked particle dispersion was obtained by performing the same operation as in steps (1) to (3) of Example 1 except that in step (3) of Example 1, adipic acid dihydrazide was changed to 0.802 g of succinic acid dihydrazide (manufactured by Tokyo Chemical Industry Co., Ltd.). The porous crosslinked particles contained in this dispersion are referred to as "chromatography carrier V4".

Next, the same step as step (4) of Example 1 was performed to obtain a filler-containing liquid for affinity chromatography. The filler contained in this liquid is referred to as "carrier having ligand immobilized thereto W4".

Example 5

A porous crosslinked particle dispersion was obtained by performing the same operations as in steps (1) to (3) of Example 1 except that in step (3) of Example 1, adipic acid dihydrazide was changed to 1.264 g of sebacic acid dihydrazide (manufactured by Tokyo Chemical Industry Co., Ltd.). The porous crosslinked particles contained in this dispersion are referred to as "chromatography carrier V5". Next, the same step as step (4) of Example 1 was performed to obtain a filler-containing liquid for affinity chromatography. The filler contained in this liquid is referred to as "carrier having ligand immobilized thereto W5".

Example 6

A porous crosslinked particle dispersion was obtained (note that N1,N1-(ethane-1,2-diyl) bis (succinic acid monoamide) was synthesized from succinic anhydride and ethylenediamine) by performing the same operation as in steps (1) to (3) of Example 1 except that in step (3) of Example 1, adipic acid dihydrazide was changed to 1.428 g of N1, N1-(ethane-1,2-diyl) bis (succinic acid monoamide) represented by the following Formula. The porous crosslinked particles contained in this dispersion are referred to as "chromatography carrier V6".

Next, the same step as step (4) of Example 1 was performed to obtain a filler-containing liquid for affinity chromatography. The filler contained in this liquid is referred to as "carrier having ligand immobilized thereto W6".

Comparative Example 1

The same operation as in steps (1) to (2) of Example 1 was performed to obtain "porous carrier 1". This carrier is referred to as "chromatography carrier X1".

Next, the same step as step (4) of Example 1 was performed to obtain a filler-containing liquid for affinity chromatography. The filler contained in this liquid is referred to as "carrier having ligand immobilized thereto Y1".

Comparative Example 2

A porous crosslinked particle dispersion was obtained by performing the same operation as in steps (1) to (3) of Example 1 except that in step (3) of Example 1, adipic acid dihydrazide was changed to 1.000 g of 3,6-dioxa-1,8-octanedithiol (manufactured by Tokyo Chemical Industry Co., Ltd.). The porous crosslinked particles contained in this dispersion are referred to as "chromatography carrier X2".

Next, the same step as step (4) of Example 1 was performed to obtain a filler-containing liquid for affinity chromatography. The filler contained in this liquid is referred to as "carrier having ligand immobilized thereto Y2."

Test Example 1 (Measurement of Consolidated Linear Flow Rate)

A column container was filled with carriers V1 to V3 and X1 to X2 obtained in each Example and Comparative Example so that the inner diameter was 16 mm and the packing height was 100 mm, and this column was connected to the AKTA pilot manufactured by GE Healthcare Biosciences. Next, pure water was started to pass at a linear flow rate of 100 cm/hr, and when a linear flow rate was gradually increased by 100 cm/hr every minute to reach 2.0 MPa, the linear flow rate was recorded as the consolidated linear flow rate. Then, the consolidated linear flow rate was evaluated according to the following criteria. The results are shown in Table 1.
(Evaluation Criteria for Consolidated Linear Flow Rate)
AAA: Consolidated linear flow rate is 3500 cm/hr or more
AA: Consolidated linear flow rate is 3100 cm/hr or more and less than 3500 cm/hr
A: Consolidated linear flow rate is 2900 cm/hr or more and less than 3100 cm/hr
B: Consolidated linear flow rate is less than 2900 cm/hr Test Example 2 (Evaluation of Shatter-Resistant Performance)

The carriers V1 to V3 and X1 to X2 obtained in each Example and Comparative Example were added to pure water so that the solid content concentration became 10% by mass, and were subjected to a circulation treatment at a discharge speed of 6 L/min 60 times using a quantitative control diaphragm pump (manufactured by TACMINA CORPORATION).

Thereafter, the carrier subjected to the circulation treatment was diluted with pure water so that the solid content concentration was about 2.5% by mass, and the circularity (=(perimeter length of a circle having the same area as a projected particle area/perimeter length of a projected particle image)×100) of each particle set to a total of 500 was measured using a flow type particle image analyzer (model number FPIA-3000) manufactured by Sysmex Corporation.

Next, a distribution of particles having a circularity of 0.95 or more (=number of particles having a circularity of 0.95 or more/number of measured particles×100) was calculated by dividing the number of particles having a circularity of 0.95 or more among all the particles to be measured by the total number of measured particles, and evaluated according to the following criteria. The results are shown in Table 1.
(Evaluation Criteria for Shatter-Resistant Performance)
AA: Distribution of particles having a circularity of 0.95 or more is 93% or more
A: Distribution of particles having a circularity of 0.95 or more is 89% or more and less than 93%
B: Distribution of particles having a circularity of 0.95 or more is less than 89%

Test Example 3 (Quantification of Protein a Binding Amount)

The amount of protein A bonded to the carriers W1 to W3 and Y1 to Y2 obtained in each Example and Comparative Example was quantified using a bicinchoninic acid (BCA) reagent.

Specifically, 1 mg of carriers W1 to W3 and Y1 to Y2 in terms of solid content, and carriers V1 to V3 and X1 to X2 before binding protein A to measure the reference value were collected in test tubes, respectively, and were infiltrated into a BCA protein assay solution manufactured by Thermo Fisher Scientific and mixed with inversion at 37° C. for 30 minutes.

Thereafter, the binding amount was calculated from the absorbance of each reaction solution (wavelength: 570 nm) and the absorbance of the calibration curve (equal to protein A bonded to the carrier). The binding amount shown in Table 2 is a value obtained by subtracting the reference value.

Test Example 4 (Evaluation of Hydrophilicity)

The hydrophilicity of the carriers W1 to W3 and Y1 to Y2 of each Example and Comparative Example was evaluated.

That is, 20 mM sodium phosphate/150 mM sodium chloride aqueous solution (pH 7.5) was passed at a linear flow rate of 300 cm/hr by using AKTAprime plus manufactured by GE Healthcare, so that each carrier was packed in a column having a capacity of 4 mL (5 mmφ×200 mm length) at a packing height of about 20 cm.

Thereafter, 1% by volume acetone/1M sodium chloride aqueous solution (100 µL) was injected into the column, and then 20 mM sodium phosphate/150 mM sodium chloride aqueous solution (pH 7.5) was passed at a linear flow rate of 300 cm/hr, so a retention time of acetone (RT (acetone)) was measured with a UV detector. Next, after a retention time of cyclohexanone (RT (cyclohexanone)) was measured in the same manner using a 1% by volume cyclohexanone/1M sodium chloride aqueous solution (100 µL), the value (CHN/ACN) of RT (cyclohexanone)/RT (acetone) was calculated, and the hydrophilicity was evaluated according to the following criteria. The results are shown in Table 2. Note that the smaller the CHN/ACN, the higher the hydrophilicity.
(Hydrophilicity Evaluation Criteria)

TABLE 1

| Chromatography carrier | | Example 1 V1 | Example 2 V2 | Example 3 V3 | Example 4 V4 | Example 5 V5 | Example 6 V6 | Comparative Example 1 X1 | Comparative Example 2 X2 |
|---|---|---|---|---|---|---|---|---|---|
| Crosslinking conditions | Types of crosslinking agents | ADH | ADH | ADH | SUDH | SDH | EBS | — | DMDO |
| | Amount of crosslinking agent used (molar times (vs. GMA)) | 0.10 | 0.25 | 0.40 | 0.10 | 0.10 | 0.10 | — | 0.10 |
| Before binding protein A | Consolidated linear flow rate (cm/hr) | 3300 Evaluation: AA | 4000 Evaluation: AAA | 4100 Evaluation: AAA | 3100 Evaluation: AA | 3400 Evaluation: AA | 2900 Evaluation: A | 2200 Evaluation: B | 2800 Evaluation: B |
| | Shatter-resistant performance (%) | 91 Evaluation: A | 94 Evaluation: AA | 95 Evaluation: AA | 90 Evaluation: A | 92 Evaluation: A | 90 Evaluation: A | 85 Evaluation: B | 88 Evaluation: B |

ADH: Adipic acid dihydrazide
SUDH: Succinic acid dihydrazide
SDH: Sebacic acid dihydrazide
EBS: N1,N1-(ethane-1,2-diyl) bis (succinic acid monoamide)
DMDO: 3,6-dioxa-1,8-octanedithiol
GMA: Glycidyl methacrylate AA: CHN/ACN is 1.060 or less
A: CHN/ACN is more than 1.060 and 1.078 or less
B: CHN/ACN is more than 1.078

Test Example 5 (Measurement of DBC)

The DBC of carriers W1 to W3 and Y1 to Y2 of each Example and Comparative Example with respect to a protein (human IgG antibody, HGG-1000 manufactured by Equitech-Bio) was measured at a linear flow rate of 300 cm/hr using AKTAprime plus manufactured by GE Healthcare. As a column container, a column container having a capacity of 4 mL (5 mmφ×200 mm length) was used, and as a protein, 5 mg/mL of protein dissolved in 20 mM sodium phosphate/150 mM sodium chloride aqueous solution (pH 7.5) was used, and the DBC was calculated from the captured amount of protein and the column packing volume at an elution peak of 10% breakthrough. The results are shown in Table 2.

Test Example 6 (Measurement of HCP)

Columns were made by filling a column container (Tricorn 10/50 column manufactured by GE Healthcare) with the carriers W1 to W3 and Y1 to Y2 of each Example and Comparative Example at a packing height of about 5 cm. The resulting columns were each connected to AKTA Prime Plus manufactured by GE Healthcare, and 20 mM sodium phosphate buffer (pH 7.5) was passed at 5 column volumes (5 times the column volume) at a flow rate of 1 mL/min and equilibrated.

Next, a CHO cell culture supernatant containing monoclonal antibody Trastuzumab was passed through the column at a flow rate of 1 mL/min with a loading amount of about 23 mg antibody/mL carrier.

Next, 20 mM sodium phosphate buffer (pH 7.5), 20 mM sodium phosphate/1 M sodium chloride buffer (pH 7.5), and 20 mM sodium phosphate buffer (pH 7.5) were sequentially passed through the columns at 5 column volumes, respectively, at a flow rate of 1 mL/min.

Thereafter, 50 mM sodium citrate buffer (pH 3.2) was passed through the column at a flow rate of 1 mL/min to elute the monoclonal antibody trapped in the column, and an elution fraction of Abs. 280>100 mAu was collected.

The antibody concentration (mg/mL) contained in the recovered fraction was measured using the spectrophotometer. In addition, the concentration (ng/mL) of the host cell protein (HCP) contained in the recovered fraction was measured using CHO HCP ELISA kit, 3G manufactured by Cygnus Technologies. Further, by dividing the concentration of the HCP by the antibody concentration, the amount of HCP per unit antibody amount was calculated and evaluated according to the following criteria. The results are shown in Table 2.

(HCP Evaluation Criteria)
A: HCP is 3300 ppm or less
B: HCP is more than 3300 ppm

TABLE 2

| Carrier having ligand immobilized thereto | | Example 1 W1 | Example 2 W2 | Example 3 W3 | Example 4 W4 | Example 5 W5 | Example 6 W6 | Comparative Example 1 Y1 | Comparative Example 2 Y2 |
|---|---|---|---|---|---|---|---|---|---|
| Crosslinking conditions | Types of cross linking agents | ADH | ADH | ADH | SUDH | SDH | EBS | — | DMDO |
| | Amount of crosslinking agent used (molar times (with reference to GMA)) | 0.10 | 0.25 | 0.40 | 0.10 | 0.10 | 0.10 | — | 0.10 |
| After binding protein A | Binding amount (mg/g) | 48 | 45 | 41 | 45 | 47 | 47 | 58 | 49 |
| | Hydrophilicity (CHN/ACN) | 1.073 | 1.066 | 1.051 | 1.068 | 1.078 | 1.062 | 1.081 | 1.092 |
| | | Evaluation: A | Evaluation: A | Evaluation: AA | Evaluation: A | Evaluation: A | Evaluation: A | Evaluation: B | Evaluation: B |
| | DBC (mg/mL) | 48 | 48 | 47 | 48 | 48 | 46 | 47 | 48 |
| | HCP (ppm) | 2800 | 2700 | 2700 | 2800 | 3000 | 2700 | 3500 | 4500 |
| | | Evaluation: A | Evaluation: A | Evaluation: A | Evaluation: A | Evaluation: A | Evaluation: A | Evaluation: B | Evaluation: B |

ADE: Adipic acid dihydrazide
SUDH: Succinic acid dihydrazide
SDH: Sebacic acid dihydrazide
EBS: N1,N1-(ethane-1,2-diyl) bis (succinic acid monoamide)
DMDO: 3,6-dioxa-1,8-octanedithiol
GMA: Glycidyl methacrylate

The invention claimed is:

1. A ligand-immobilizing carrier, comprising:
a chromatography carrier; and
an antibody affinity ligand immobilized to the chromatography carrier,
wherein the chromatography carrier comprises a polymer having a structural unit (A) of formula (9) and a structural unit (B) of formula (10), and wherein a residue of a functional group capable of immobilizing a ligand in the structural unit (B) is crosslinked by a crosslinked structure of formula (2-1) or (2-4), the formula (9) is where $R^8$ is a hydrogen atom or a methyl group, $R^9$ is a single bond or a divalent linking group, and $Z^1$ is a functional group capable of immobilizing a ligand, and the formula (10) is where $R^{10}$ is a hydrogen atom or a methyl group, $R^{11}$ is a single bond or a divalent linking group, $Z^2$ is a residue of a functional group capable of immobilizing a ligand, and ** is a bond that is bonded to the crosslinked structure of the formula (2-1) or (2-4)

where $R^2$ is a single bond or a divalent linking group, * is a chemical bond, and each of $R^{4a}$ and $R^{4b}$ is independently a divalent linking group.

2. The ligand-immobilizing carrier of claim 1, wherein the crosslinked structure has the formula (2-1).

3. The ligand-immobilizing carrier of claim 1, wherein the polymer further comprises a structural unit derived from an aromatic vinyl-based crosslinkable monomer.

4. The ligand-immobilizing carrier of claim 1, wherein the antibody affinity ligand is an immunoglobulin-binding protein.

5. The ligand-immobilizing carrier of claim 1, wherein $R^2$ is (i) a divalent hydrocarbon group having 1 to 40 carbon atoms or (ii) a group comprising an ether bond, an amide bond, an ester bond, or two or more of any of these, between carbon-carbon atoms of a divalent hydrocarbon group having 2 to 40 carbon atoms.

6. The ligand-immobilizing carrier of claim 1, wherein $R^2$ is (i) an alkanediyl group having 1 to 40 carbon atoms or (ii) a group comprising an ether bond, an amide bond, an ester bond, or two or more of any of these, between carbon-carbon atoms of an alkanediyl group having 2 to 40 carbon atoms.

7. The ligand-immobilizing carrier of claim 1, wherein the antibody affinity ligand is protein A, protein G, or protein L.

8. The ligand-immobilizing carrier of claim 1, wherein the chromatography carrier is a particulate chromatography carrier.

9. The ligand-immobilizing carrier of claim 1, wherein the chromatography carrier is a porous chromatography carrier.

10. The ligand-immobilizing carrier of claim 2, wherein the polymer further comprises a structural unit derived from an aromatic vinyl-based crosslinkable monomer.

11. The ligand-immobilizing carrier of claim 2, wherein the antibody affinity ligand is an immunoglobulin-binding protein.

12. The ligand-immobilizing carrier of claim 2, wherein $R^2$ is (i) a divalent hydrocarbon group having 1 to 40 carbon atoms or (ii) a group comprising an ether bond, an amide bond, an ester bond, or two or more of any of these, between carbon-carbon atoms of a divalent hydrocarbon group having 2 to 40 carbon atoms.

13. The ligand-immobilizing carrier of claim 2, wherein $R^2$ is (i) an alkanediyl group having 1 to 40 carbon atoms or (ii) a group comprising an ether bond, an amide bond, an ester bond, or two or more of any of these, between carbon-carbon atoms of an alkanediyl group having 2 to 40 carbon atoms.

14. The ligand-immobilizing carrier of claim 2, wherein the antibody affinity ligand is protein A, protein G, or protein L.

15. The ligand-immobilizing carrier of claim 2, wherein the chromatography carrier is a particulate chromatography carrier.

16. The ligand-immobilizing carrier of claim 2, wherein the chromatography carrier is a porous chromatography carrier.

17. A chromatography column, comprising:
the ligand-immobilizing carrier recited in claim 1; and
a column container,
wherein the carrier is comprised in the column container.

18. A method for purifying a target substance by chromatography, comprising:
bringing the ligand-immobilizing carrier recited in claim 1 into contact with the target substance.

19. A method for purifying a target substance by chromatography, comprising:
bringing the ligand-immobilizing carrier recited in claim 1 into contact with a sample containing the target substance.

* * * * *